(12) United States Patent
DiFoggio et al.

(10) Patent No.: US 7,299,136 B2
(45) Date of Patent: Nov. 20, 2007

(54) METHOD AND APPARATUS FOR ESTIMATING OF FLUID CONTAMINATION DOWNHOLE

(75) Inventors: Rocco DiFoggio, Houston, TX (US); Bernardo Pohl, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 11/207,398

(22) Filed: Aug. 19, 2005

(65) Prior Publication Data

US 2006/0236758 A1 Oct. 26, 2006

Related U.S. Application Data

(63) Continuation-in-part of application No. 11/112,626, filed on Apr. 22, 2005, now abandoned.

(51) Int. Cl.
*G01N 31/00* (2006.01)

(52) U.S. Cl. ..................................................... 702/22

(58) Field of Classification Search ............ 702/9, 702/11, 12, 14, 22–25, 30, 35, 50, 66, 73, 702/79, 100, 116, 141, 168, 183; 250/256, 250/269.1; 73/152.04, 152.05, 152.08, 152.09
See application file for complete search history.

(56) References Cited

U.S. PATENT DOCUMENTS

| | | | |
|---|---|---|---|
| 5,223,715 A * | 6/1993 | Taylor | .................. 250/343 |
| 6,274,865 B1 | 8/2001 | Schroer et al. | ........... 250/269.1 |
| 6,343,507 B1 * | 2/2002 | Felling et al. | ............ 73/152.19 |
| 6,350,986 B1 * | 2/2002 | Mullins et al. | ........... 250/269.1 |
| 6,714,872 B2 | 3/2004 | DiFoggio et al. | .............. 702/12 |
| 6,956,204 B2 * | 10/2005 | Dong et al. | .................. 250/256 |
| 2004/0000400 A1 | 1/2004 | Fujisawa et al. | ........ 166/250.01 |

OTHER PUBLICATIONS

Lee et al., Fluid Sampling From Damaged Formations, SPE 39817, 1998, pp. 565-570.
Sarkar et al., Adverse Effects Of Poor Mud Cake Quality: A Supercharging And Fluid Sampling Study, SPE 48958, 1998, pp. 1-12.
Mullins et al., Real-Time Quantification Of OBM Filtrate Contamination During Openhole Wireline Sampling By Optical Spectroscopy, SPWLA 41st Annual Logging Symposium, Jun. 4-7, 2000, pp. 1-10.

* cited by examiner

*Primary Examiner*—Hal Wachsman
*Assistant Examiner*—Mohamed Charioui
(74) *Attorney, Agent, or Firm*—Madan, Mossman & Sriram, P.C.

(57) ABSTRACT

The present invention provides method and apparatus for quantifying sample clean up in real time by providing curve-fitting measurements of optical or other physical properties of fluid downhole. Fluid is extracted from the formation surrounding a borehole. As fluid continues to be extracted the composition of the extracted fluid changes, altering the measured values of optical and physical properties of the fluid. Measurements are made of optical or physical properties of the sampled fluid, analysis is performed on the acquired measured data points.

19 Claims, 6 Drawing Sheets

510

FIT DATA USING A NON-ASYMPTOTIC EQUATION OF THE FORM: $A = A_0 - h(t)$
where, as $t \to \infty$, $h(t)$ does NOT go to zero.
Example 1: $A = A_0 - A_1 \Sigma t^x$, where $x = -n$ to $+m$, where $m > 0$
Example 2: $A = A_0 - A_1 [ t^{-P} + k^{-1} \sin(\omega t) ]$

410 ─┐

> PREFORM A PIECEWISE NON-ASYMPTOTIC CURVE FIT TO DATA TO DETERMINE SMOOTHED VALUES AND DATA SLOPES AT CENTERS OF EACH SEGMENT
>
> REGRESS ln(dA/dt) AGAINST ln(t) TO OBTAIN A STRAIGHT-LINE REGRESSION SLOPE AND INTERCEPT
>
> COMPUTE $f_{tp}$ FROM THIS STRAIGHT-LINE REGRESSION SLOPE AND INTERCEPT AND FROM AVERAGES OF $A(t)$ AND $A_1 t^{-p}$ AT A PLURALITY OF TIMES

> FIT DATA USING A NON-ASYMPTOTIC EQUATION OF THE FORM: $A = A_0 - h(t)$
> where, as $t \to \infty$, $h(t)$ does NOT go to zero.
> Example 1: $A = A_0 - A_1 \Sigma t^x$, where $x = -n$ to $+m$, where $m > 0$
> Example 2: $A = A_0 - A_1 [t^{-p} + k^{-1} \sin(\omega t)]$

> DO PATTERN RECOGNITION FOR A TRIAL-AND-ERROR ESTIMATE OF (NOT A DIRECT CALCULATION OF) $A_0$.
>
> TEST VARIOUS $A_0$ VALUES: $A, A+\varepsilon, A+2\varepsilon, \ldots, A_{MAX}$
>
> USE THAT $A_0$ FOR WHICH THE PLOTTED DATA MOST RESEMBLES A STRAIGHT LINE

Estimate $f_{tp}$ from the ratio of the rate of change of A to the value of A using an equation of the form, $$f_{tp} = [1 - A^{-1}(dA/dt)\, h(t)\, (dh/dt)^{-1}]^{-1}$$

Example 1: Estimate $f_{tp}$ from the equation, $$f_{tp} = [1 + A^{-1}(dA/dt)\, tp^{-1}]^{-1}$$

Example 2: Estimate $f_{tp}$ from the equation, $$f_{tp} = [1 + (12/5)\, A^{-1}(dA/dt)\, t]^{-1}$$

PERFORM A FIT TO ABSORBANCE DIFFERENCES RATHER THAN TO ABSORBANCES THEMSELVES.

(ABSORBANCE DIFFERENCES ARE INSENSITIVE TO BASELINE OFFSETS SUCH AS THOSE CAUSED BY PASSING SAND PARTICLES)

USE THIS APPROACH EITHER IN CONJUNCTION WITH OR INDEPENDENTLY OF THE METHODS DESCRIBED IN THE PREVIOUS FIGURES

FIG. 10

METHOD AND APPARATUS FOR ESTIMATING OF FLUID CONTAMINATION DOWNHOLE

This application is a Continuation-In-Part of the U.S. patent application Ser. No. 11/112,626 filed on Apr. 22, 2005, now abandoned.

BACKGROUND OF THE INVENTION

1. Field of the Invention

The invention relates generally to a method and apparatus for quantifying fluid contamination as an indication of sample cleanup in real time in a wellbore environment. Specifically, the invention is a method and apparatus for measurement of physical properties of fluid being pumped from a formation surrounding a wellbore by a wireline or monitoring while drilling tool to estimate sample cleanup or to predict the time at which a sample having a desired purity can be obtained.

2. Summary of the Related Art

In wellbore exploration, typically drilling muds such as oil-based muds and synthetic-based muds or water-based muds are used. The filtrates from these muds generally invade the formation through the borehole wall to an extent, meaning that this filtrate must be removed from the formation in order to access the formation fluids. Open hole sampling is an effective way to acquire representative reservoir fluids. Sample acquisition allows determination of critical information for assessing the economic value of reserves. In addition, optimal production strategies can be designed to handle these complex fluids. In openhole sampling, initially, the flow from the formation contains considerable filtrate, but as this filtrate is drained from the formation, the flow increasingly becomes richer in formation fluid. That is, the sampled flow from the formation contains a higher percentage of formation fluid as pumping continues.

It is well known that fluid being pumped from a wellbore undergoes a clean-up process in which the purity of the sample increases over time as filtrate is gradually removed from the formation and less filtrate appears in the sample. Here, $f_p$ is defined to be the fraction of purity and $f_c$ to be the fraction of contamination, where $f_p+f_c=1$. As the composition of the sampled formation fluid changes, so do the optical and physical properties of the sampled fluid, such as optical absorption, fluorescence, refractive index, viscosity, density, sound speed, and bulk modulus. A number of different measurements are used to determine various optical and physical properties of a fluid downhole in real time. Measuring these properties of the fluid therefore provides qualitative insight into a fluid sample's purity but does not provide a quantitative value, $f_p$, for the fluid sample's purity. There has been a mistaken notion that, after pumping for a long time, the fraction of fluid contamination necessarily drops to zero. Actually, in many cases where, after a long pumping time, some optical or physical property was not substantially changing yet the fraction of contamination (as subsequently determined in a surface lab) was far from zero and was even as high as 45%. In that case, the terminal purity was only 55%.

At long pumping times, a dynamic equilibrium can be reached in which a fluid sample being withdrawn from a tapped zone cleans up at the same rate that it is being recontaminated from above and below that tapped zone. Thus, even though a downhole measured property (OD, etc.) has substantially stopped changing, the sample is still not at 100% purity. This dynamic equilibrium depends on various factors such as the ratio of the vertical to horizontal permeability. Therefore, we define $f_{tp}$ to be the fraction of the terminal purity, where the terminal purity is the purity achieved at very long pumping times and is usually less than 100%. All that we can estimate by monitoring changes in OD or some other property over time (or over volume pumped) is the fraction of the terminal purity, $f_{tp}$, but not the fraction of formation-fluid purity, $f_p$.

When extracting fluids from a formation, it is desirable to quantify the cleanup progress, that is, the degree of filtrate contamination in real time. If it is known that there is too much filtrate contamination in the sample (more than about 5% or 10%), then there is no reason to collect the formation fluid sample in a sample tank until the contamination level drops to an acceptable level. On the other hand, if by pumping for a very long time, it is possible to achieve only slightly better contamination level, an operator ends up wasting very expensive rig time and also risks the very costly possibility of allowing a tool to become stuck in the wellbore. Thus, there is a need to determine how long one must pump to obtain a suitable purity sample from the formation.

When pumping first begins, the fluid being pumped contains a large amount of mud filtrate contamination and the fluid filtrate percentage is decreasing at the fastest rate. This process of decreasing fluid filtrate contamination is referred to as sample clean up. Later, the pumped fluid contains less contamination and the fluid filtrate percentage decreases at a slower rate. Mullins, et. al. published paper on curve fitting of a sample's absorbance versus time to monitor clean up in real time, entitled "Real Time Determination of Filtrate Contamination During Openhole Wireline Sampling by Optical Spectroscopy," SPWLA, 41$^{st}$ Annual Meeting, Dallas, Tex., June, 2000. The U.S. Pat. Nos. 6,274,865 and 6,350,986 also discuss such curve fitting.

In this paper, Mullins et al. assume that the rate of sample cleanup as measured by observing optical density progresses as $t^{-5/12}$ where t is time. This clean up rate is based on empirical experience in the Gulf of Mexico and elsewhere. However, Mullins et al. also states that, for extended pumping durations, that the sample cleanup rate for shallow invasion progresses as $t^{-1/3}$ and that the cleanup rate for deeper invasions progresses as $t^{-2/3}$. Clearly, an assumption of a sample clean rate of $t^{-5/12}$ can be rigid and inapplicable to real time situations. Moreover, using time as a fitting parameter necessarily assumes a constant pumping rate. Another problem with monitoring sample clean up over time by looking at optical absorption over time is that sand particles and other particulates can cause considerable scattering, which causes the absorption values measured over time to "jump" and appear noisy. Thus, there is a need for a more flexible model regarding the estimation of formation cleanup based on fluid properties and characteristics for downhole pumping in real time.

SUMMARY OF THE INVENTION

The present invention provides a method and apparatus of quantifying sample clean up in real time from measurement data over time (or over volume) of some optical or physical properties of fluid samples taken from a formation surrounding a borehole. Sample fluid is extracted from the formation surrounding the borehole. As fluid continues to be extracted from the formation, the composition of the sampled fluid changes, altering the measured values of an optical or physical property for the sampled fluid.

In a first aspect of the present invention, a method and apparatus are provided that fit fluid measurement data to a non-asymptotic curve. One example of a non-asymptotic curve is a curve (e.g., a power series approximation), which provides an improved fit to the data over the typical pumping time and, which can also be successfully extrapolated to several times that pumping time, but which approaches plus or minus infinity at infinite times. Another example of a non-asymptotic curve is an equation that has an oscillatory component such as a sine wave, which never reaches a fixed limit. The sine wave can be adjusted in frequency, phase and amplitude to provide an improved fit to pulses in the monitored response that are associated with each stroke of the pump. In a third aspect of the invention, a method and apparatus are provided that perform pattern recognition of a straight line to a best fit of the measured data in log-log space.

For best performance, spikes in the data are removed first. The remaining data are piecewise smoothed over a rolling interval of 100 or more neighboring points using a smoothing function. For example, a fit can be performed for absorbance over a rolling time segment using a non-asymptotic fitting equation such as, $A=b_0+b_1 t+b_2 t^2$. Then, by calculus, $A'=dA/dt=b_1+2b_2 t$ and $A'/A=(b_1+2b_2 t)/(b_0+b_1 t+b_2 t^2)$. Then, for an equation of the form, $A(t)=A_0-A_1 t^{-p}$, one can do a linear regression of $\ln(dA/dt)$ against $\ln(t)$ to obtain the slope and intercept and from these calculate, $-p=(1+\text{Slope})$ and $-A_1=\exp(\text{Intercept}-\ln(1+\text{Slope}))$. In this way, there is not an assumption of a value of $-5/12$, of $-2/3$, or of any other fixed value for $-p$. Instead, one can estimate $f_{tp}=A/A_0$ from the best-fit values for p and $A_1$, and from twice the average of $A(t)$ and $A_1 t^{-p}$ at a plurality of times.

The method and apparatus of the present invention can use a data-fitting equation such as $\log(1-f_{tp})=(-p)\log(t)+\log(A_1/A_0)$, which is the equation of a straight line that has no (Y=constant) asymptote, except for the meaningless case of p=0. The method and apparatus perform a series of regressions using different estimates of $A_0$ but do not actually calculate $A_0$, itself. For example, one can start with the current value, A, at a time t, as the first estimate of $A_0$, then proceed to a slightly higher value of $A+\epsilon$, then to an even higher value of $A+2\epsilon$, and so on. The $A_0$ value for which the fit to the measured data is closest to the shape of a straight line (based on the highest coefficient of determination, or R-squared value) then becomes the best estimate of an $A_0$ value. In a third aspect the method and apparatus of the present invention a method and apparatus are provided that fit a differentiable curve to measurement data or physical property data derived from the measurement data. The present invention then estimates $f_{tp}$ from the ratio of (dA/dt) to A. In a fifth aspect of the present invention a method and apparatus are provided that fit an asymptotic curve to difference of two responses such as the difference of two absorbances associated with different wavelengths (optical channels) rather than to an absorbance itself. Using an absorbance difference removes the baseline offsets caused by passing sand particles or bubbles.

BRIEF DESCRIPTION OF THE FIGURES

Other objects and advantages of the invention will become apparent upon reading the following detailed description and upon reference to the accompanying drawings in which:

FIGS. 3-10 are charts of functions performed in embodiments of the invention;

DETAILED DESCRIPTION OF THE INVENTION

Figure 1:
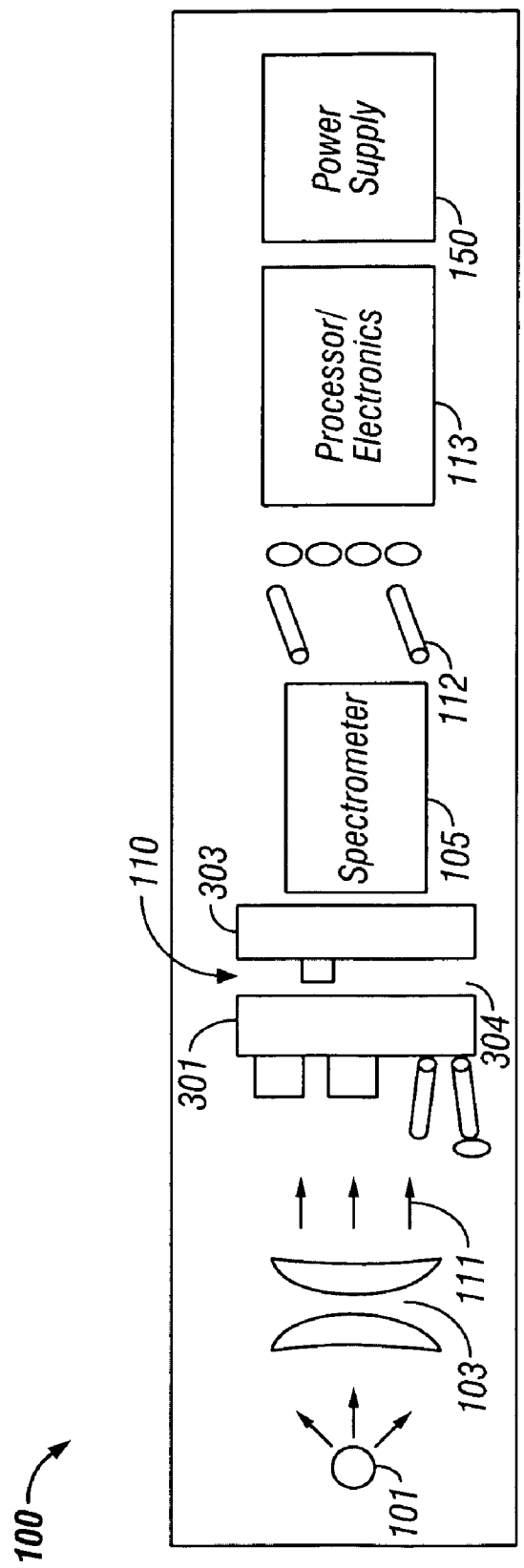
FIG. 1 is a diagram of the Fluid Characterization Module.

FIG. 1 illustrates a schematic representation for a downhole fluid characterization module for obtaining and analyzing optical measurement data. A light source 101 (e.g. tungsten light bulb) emits light toward a fluid 110. The light can be collimated by a collimating lens device 103 lying between the light source and the fluid 110. The collimated light 111 is incident generally perpendicular to a first sapphire window 301 adjacent sample 110. Sapphire windows 301 and 303 lie generally perpendicular to the collimated beam of light and are separated by a gap or channel 304 enabling a fluid 110 to flow between them. An optical property of the fluid, for example, including but not limited to reflectance, absorbance and fluorescence of light from the fluid is measured over time by an optical sensor, such as but not limited to a spectrometer 105. A processor is provided to estimate fluid properties in the processor 113 from the optical measurements. The processor 113 includes memory. The existing tools (FIG. 1) can be fitted with a UV or infrared light source 112, which can be turned on when the tungsten light source 101 is turned off. The same spectrometer, for example, comprising single wavelength filters over photodiodes, enables collecting the crude oil fluorescence and infrared spectra. The processor 113 includes memory and performs calculations using equations to estimate fluid properties, such as percent contamination, from the optical measurements for the fluid as described herein.

Figure 2:
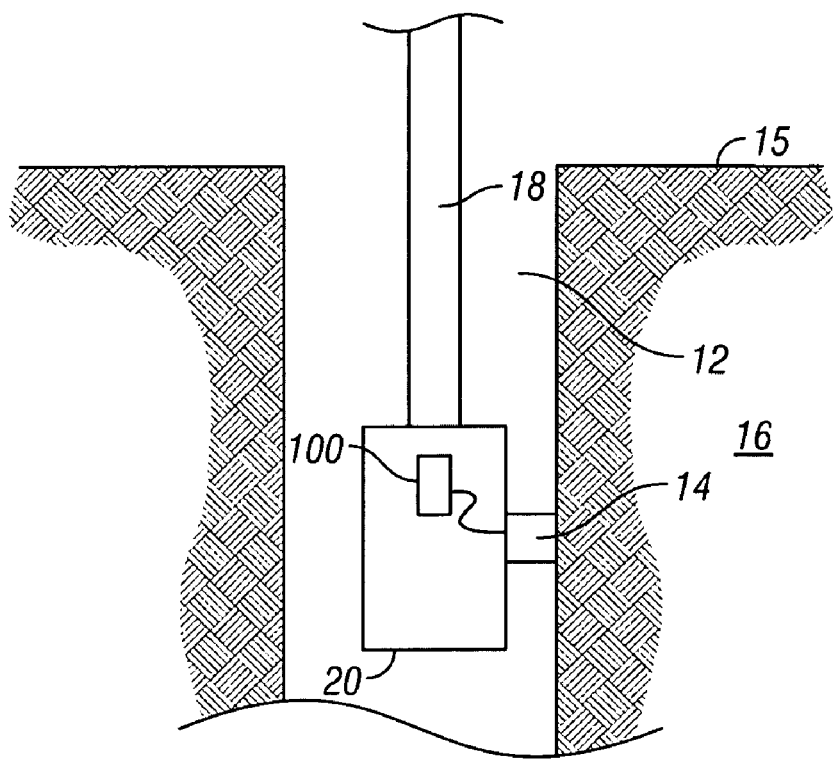
FIG. 2 is an illustration an embodiment of the present invention deployed in a borehole using a plurality of sources and sensors.
Figure 11:
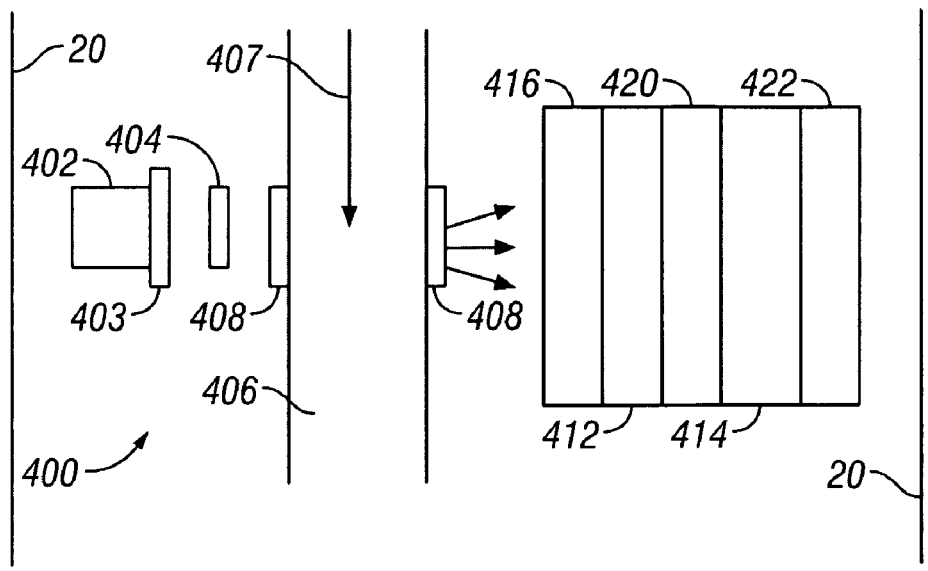
FIG. 11 is an illustration of an embodiment of the invention using an acoustic transducer.
Figure 12:
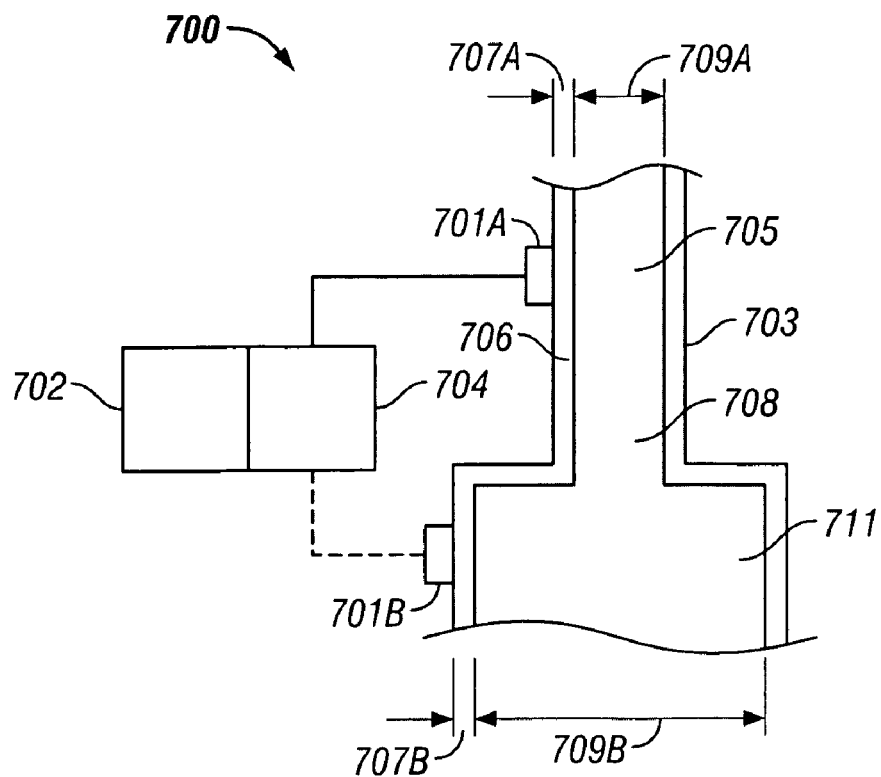
FIG. 12 is an illustration of an embodiment of the invention using a pyroelectric array.

As shown in FIG. 2, additional measurements from additional sources and sensors can be added, including but not limited to a flexural mechanical resonator, acoustic transducer, pyroelectric array and infrared light source. More detailed schematics of the acoustic transducer and the pyroelectric array are shown in FIGS. 11 and 12. These additional sources and sensors can be provided for measurements of fluid parameters including but not limited to viscosity, density, sound speed, fluorescence, attenuated total reflectance, refractive index and bulk modulus. Additional description on the operation of these sources and sensors can be found in co-pending patent application Ser. No. 11/051,388 filed on Feb. 4, 2005, entitled, A Method and Apparatus for Analyzing a Downhole Fluid Using a Thermal Detector, which is hereby incorporated by reference in its entirety; U.S. patent application Ser. No. 10/144,965 filed on May 14, 2002 entitled Method and apparatus for Downhole Fluid Characterization Using Flexural Mechanical Resonators, which is hereby incorporated by reference in its entirety; and Ser. No. 10/051,388 filed on Mar. 16, 2004 entitled Method and Apparatus for Acoustic Pulse Decay Density Determination, which is hereby incorporated by reference in its entirety. These measurements can be monitored over time to estimate fractional terminal purity as discussed below.

FIG. 2 illustrates an embodiment of the present invention 100 deployed in a borehole 12 drilled from the surface 15 and formed in a formation 16. A probe 14 is provided for extraction of fluid from the formation. The present invention is contained in a downhole tool 20. The downhole tool is deployed from a wireline or drill string 18. One of the problems with monitoring the cleanup over time by looking at the optical absorption over time (over a 2 mm path length) is that sand particles and other particulates cause considerable scattering, which makes the absorption over time "jump" a lot and look very noisy. Monitoring cleanup over time by monitoring refractive index (which is an interface-based technique) is less sensitive to particulates in the fluid stream because one is only looking at a thin layer of fluid that is in direct contact (at the interface) with the sapphire window. Similarly, for crude oils, fluorescence only sees a thin layer of crude oil near the window and therefore, it is very insensitive to particulates in the stream.

Prior systems used the functional form for the cleanup approximated by $\ln(OD)=C-D/t^p$ discussed below. Some prior systems calculated the percentage of contamination by assuming that, upon reaching asymptotic optical absorbance, the sample had achieved zero contamination. Other prior systems, however, assumed that a dynamic equilibrium can be reached between fluid clean up and continued filtrate incursion, depending on the ratio of vertical to horizontal permeability and other factors. Thus, the contamination may not drop to zero, but only to some minimum value, even after very long pumping times. That is, the terminal contamination level represents the minimum contamination but, not necessarily, zero contamination.

As the composition of the sampled formation fluid properties change, so do the optical and physical properties of the sampled fluid, such as optical absorption, fluorescence, refractive index, viscosity, density, sound speed, and bulk modulus. These properties can be monitored to estimate the fraction of terminal purity, which is the degree of formation fluid clean up. As an example of formation fluid clean-up, simulation results and actual field data for optical density can be fitted to forms such as, $Y=mX^{-p}+b$ or $\ln(Y)=mX^{-p}+b$. Using the sample contamination concentration as Y and the pumping time as X, simulation results fit these forms well, especially the logarithmic form. Because the optical density (OD) is an indicator of clean-up, the OD data can be used as Y and the pumping time can be used as X. If the pumping speed changes many times during the course of clean-up, the cumulative volume pumped is used as X instead of time.

A small p value indicates that clean-up process is slow and it will take longer to obtain a quality sample, while a large p value indicates that the clean-up process will be faster and the chance for obtaining a sample of the desired purity is high. The value of b is used as an indicator for clean-up to the best sample quality achievable (the asymptotic value). By comparing the current OD value with the b value, the current sample contamination percentage is obtained. The future sample quality is estimated using the fitted values of m, p, and b, and a decision can be made as to whether to continue or to stop the pumping process if the estimated future sample quality is deemed insufficient.

The power of X, which is −p, (where p is a positive number) can be used as an indicator of the rapidity of the clean-up process. Consequently, when the p value is small, and the calculated current contamination is high, there will be little chance of obtaining a high quality sample and it will take a long time, perhaps too long to obtain the desired sample purity.

When the invasion profile is gradual, meaning a transition zone is present instead of sharp invasion boundary, the value of p decreases below 1.0. The value of p depends on the thickness of the transition zone between the region of filtrate and region of formation fluid. The thicker the transition zone, the lower the p value. This gradual transition has a similar effect to that of deep invasion. When the invasion is deep, then the clean fluid from the fresh zone will be mixed deep, with the filtrate while it flows toward the probe. Hence a deep invasion will have a thick transition zone, and clean-up for that zone will take a long time.

Formation damage can also affect the clean-up process. The clean-up can be improved when the formation near the wellbore is damaged or when the near wellbore formation permeability is less than the true formation permeability due to the small particle invasion.

The functional form (see, e.g., U.S. Pat. No. 6,714,872) that is a best fit to simulation data regardless of invasion depth or formation damage is $OD=\exp(mt^{-p}+b)$, so that at longer times, the OD stops changing because the time-dependent term goes to zero as time goes to infinity. That form is equivalent to the form, $\ln(OD)=C-D/t\hat{}p$ where C=b, m=−D, and p is a positive number. Curve fitting of sample clean-up using the form of $$\ln(Y)=mX^{-p}+B$$

where Y=optical or physical properties such as absorbance or fluorescence at some wavelength as the sample as it cleans up, X=Time since started pumping sample or, more correctly, the cumulative volume pumped, when the volumetric flow rate is not constant.

Applying the functional form $\ln(OD)=A*1/Time^n+B$ to simulation results, shows that: a) In a simple system with no permeability damage and a sharply-defined filtration zone (100% filtrate zone followed by 0% zone), the n value is 1.1; b) Adding permeability damage to system, speeds up the cleaning process, and the n value is 1.3; c) Using a gradual filtrate contamination, in which contamination decreases as moving away from wellbore (that is 100, 80, 60 . . . and 0%) then the n value is 0.75; d) Adding damage to the system (c), then the n value is 1.0; and e) Adding a permeability change due to formation damage, then the n value can vary from 0.25 to 0.5. Fitting formation clean-up simulation results and some field data (optical density) to the above functional form, the following findings are provided.

Using the sample contamination concentration as Y and the cumulative pump-volume as X, simulation results fit the form very well. Because the optical density (OD) is an indicator of clean-up, the OD data can be used as Y and pump-time can be used as X. If the pumping speed changes many times during the course of clean-up, the cumulative volume pumped should be used as X instead of time. The power of X, which is −p (where p is a positive number), can be used as an indicator for the clean-up process. For a nominal invasion of 6 inches or less, p is near 1.0-1.1. When the invasion profile is gradual, this indicates that there is a transition zone instead of a sharp invasion boundary, and p decreases below 1.0. The p value will depend on the thickness of the transition zone, the thicker the zone, the lower the p value. A similar effect is found for deep invasion. When the invasion is deep, then the clean fluid from the fresh zone will be mixed with the filtrate while it flows toward the probe. Hence the deep invasion will have a thick transition zone, and it will take a longer time to clean-up that zone.

When the formation near the wellbore is damaged, that is the near wellbore formation permeability is less than the true formation permeability due to the small particle invasion, the clean-up can be improved as discussed in papers in the Society for Petroleum Engineers, papers SPE 39817 and SPE 48958. The formation anisotropy also helps the clean-up process (see SPE papers, SPE 39817 and SPE 48958). When there is a damage or a formation anisotropy, the p value increases above 1.0-1.1 up to 1.3-1.4. Hence a small p value indicates that the clean-up process will be slow and will take longer to get a quality sample of the desired purity.

A high p value indicates that the clean-up process will occur quickly and the chance for a good quality sample is high. The B value can be used as the best sample quality achieved. By taking the ratio of the current OD value to the B value, the fraction of the cleanest possible sample is obtained. Using the fitted values of m, p, and B, the future sample quality can be estimated and a decision as to whether to continue or stop the sample pumping process can be made. When the p value is small, and the calculated current contamination is high, there will be little chance of obtaining a high quality sample of the desired purity and it will take an infeasible amount of time to obtain the desired sample.

It is primarily the aromatic and polynuclear aromatics molecules that fluoresce. That is why, crude oil usually fluoresces much more than does the filtrate of oil based mud (OBM). For environmental reasons, synthetic OBMs are designed to be as aromatic free as possible but they may pick up some aromatic contamination from drilling or they may have small amounts of aromatic emulsifiers or fluid loss control materials added to them. Also, the filtrate of water-based mud has little or no fluorescence because water itself is non-fluorescing. Some compounds that dissolve in water may fluoresce. Furthermore, one could deliberately add fluorescent compounds to water based or oil based mud as fluorescent tracers.

In the specific case where the property being fit is a function of the optical absorption, certain particularly useful functions can be selected for the absorption. One such function is the ratio of a baseline-adjusted oil peak to a baseline-adjusted water peak or its inverse. This function is particularly useful in monitoring the cleanup from water based mud filtrate to native crude oil. Its inverse is particularly useful in monitoring the cleanup from oil based much filtrate to connate water, when it is desired to collect a sample of water.

The baseline-adjusted oil peak is an oil peak channel (near 1740 nm) minus a nearby low-absorbance "baseline reference" channel (e.g. channels at 1300 or 1600 nm). The baseline-adjusted water peak is a water peak channel (near 1420 or 1935 nm) minus a nearby low-absorbance "baseline reference" channel (e.g. channels at 1300 or 1600 nm). Substituting time equals infinity into our forecasting model enables estimation of the limiting value of property, P, at infinite time. Dividing the current value of property, P, by its forecasted terminal value yields the fraction of terminal purity.

In a first embodiment of the present invention, the method and apparatus of the present invention fit fluid measurement data to a non-asymptotic curve. One example of a non-asymptotic curve is a curve which provides an improved fit to the data over the typical pumping time and, which can also be successfully extrapolated to several times that pumping time, but which approaches plus or minus infinity at infinite times, such as a power series approximation. Another example of a non-asymptotic curve is an equation that has an oscillatory component such as a sine wave, which never reaches a fixed limit. The sine wave can be adjusted in frequency, phase and amplitude to provide an improved fit to pulses in the monitored response that are associated with each stroke of the pump.

In a second embodiment, the method and apparatus use pattern recognition. That is, the method and apparatus of the present invention use an equation such as $\log(1-f_{tp})=(-p)\log(t)+\log(A_1/A_0)$. The method and apparatus then perform a series of different estimates of the terminal purity or terminal value for a physical property of the fluid is represented by $A_0$, where $A_0$ starting with $A_1$, $A+\epsilon$, $A+2\epsilon$, etc. The $A_0$ value for which the fit to the data is closest to the shape of a straight line (based on the R-squared value) becomes the best estimate of $A_0$. In a third embodiment the method and apparatus of the present invention fits a differentiable curve to measurement data or physical property data derived from the measurement data. The present invention then estimates $A/A_0$ from the ratio of $(dA/dt)$ to $A$. In a fourth embodiment, the present invention fits an asymptotic curve to absorbance differences of nearby optical channels (wavelengths) rather than to absorbance itself. The absorbance differences remove baseline offsets caused by passing sand particles or bubbles.

In the conventional approach to formation contamination, equations 1 and 3 are applicable.

$$A = A_0 - A_1 t^{-5/12} \text{ where } A_0 > 0, A_1 > 0, \qquad \text{Eq. 1}$$
$$\lim_{t \to \infty} A = A_0$$

Instead of time, t, volume, V could be used. One could also generalize to the case where the best fitting power, p, is calculated instead of assumed.

$$A = A_0 - A_1 t^{-p} \text{ where } A_0 > 0, A_1 > 0, p > 0 \qquad \text{Eq. 2}$$
$$\lim_{t \to \infty} A = A_0$$

$$f_{tp} = A/A_0 = \text{fraction of terminal absorbance, } A_0, \text{ which is achieved when absorbance is } A. \qquad \text{Eq. 3}$$

Only in those cases where $A_0$ is the absorbance of pure crude oil does $f_{tp}$=fraction of terminal purity also equal $f_p$=fraction of purity.

$$1-f_{tp}=[1-(A/A_0)]=\text{fraction away from terminal absorbance.} \qquad \text{Eq. 4}$$

For Eq. 1, the conventional approach finds best $A_0$, $A_1$ using a linear least squares fit to the N data points, $(A_i, t_i^{-5/12})$, where i=1, N. For Eq. 2, one finds best $A_0$, $A_1$ using a linear least squares fit to the N data points, $(A_i, t_i^{-p})$, where i=1, N after one assumes or finds a best fit value for p as described elsewhere in this invention.

Figure 3:
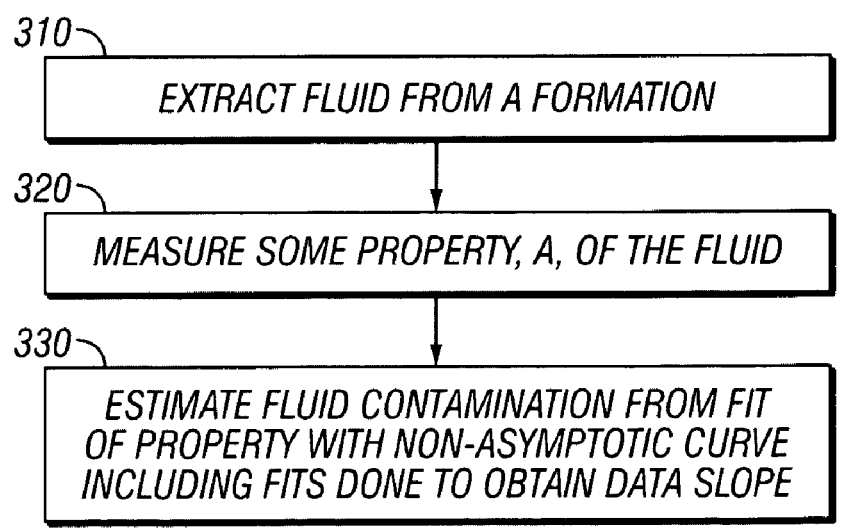

Turning now to FIGS. 3-10, various functions performed in embodiments for the invention are depicted. As shown in FIG. 3, in one example of the present invention fluid is extracted from a formation 310. A property of the fluid is measure 320 from which an estimate of fluid contamination is made from a fit of the property with a non-asymptotic curve including fits performed to obtain data slope 330.

Although the discussion below uses elapsed time as the dependent variable, it is understood that the volume of pumped fluid or some other parameter could also be used. As shown in FIG. 4, in an embodiment of the present invention the present invention performs a piecewise non-asymptotic curve fit to data to determine smoothed values and data slopes at centers of each segment. A regression is performed on the logarithm of the derivative of the data over time against the logarithm of time to obtain a straight-line regression slope and intercept. A value for fractional terminal purity ftp is estimated from the straight-line regression slope and intercept and from averages of $A(t)$ and $A_1 t^{-p}$ at a plurality of times. For example, a method and apparatus are provided to fit absorbance over a rolling time segment using a non-asymptotic equation such as the power series, $A=b_0+b_1 t+b_2 t^2$. Then, by calculus, $A'=dA/dt=b_1+2b_2 t$ and $A'/A=(b_1+2b_2 t)/(b_0+b_1 t+b_2 t^2)$. For an equation of the form, $A(t)=A_0-A_1 t^{-p}$, one can perform a straight-line regression of $\ln(dA/dt)$ against $\ln(t)$ to obtain the best-fit line's slope and intercept and calculate best-fit values, $-p=(1+\text{Slope})$ and $-A_1=\exp(\text{Intercept}-\ln(1+\text{Slope}))$. In this way, one does not need to assume a value of $-5/12$, or $-2/3$, or of any other fixed value for $-p$. Instead, one can estimate $f_{tp}=A/A_0$ from the best-fit values for $p$ and $A_1$, and from twice the average of $A(t)$ and $A_1 t^{-p}$ at a plurality of times 410.

As shown in FIG. 5, in the second embodiment of the present invention, a method and apparatus are provided that use a non-asymptotic curve to fit the data 510. In this embodiment, the method and apparatus fit a modified version of Eq. 1 to data, wherein the modified equation does not approach an asymptote at infinite time such as the examples shown in Equations 8 and 9 below, using the form $A=A_0-h(t)$ where $t \to \infty$ and $h(t)$ does not go to zero.

$$A=A_0-A_1 \Sigma t^x, \text{ where } x=-n \text{ to } +m, \text{ where } m>0. \quad \text{Eq. 8}$$

$$A=A_0-A_1[t^{-p}+k^{-1}\sin(\omega t)]. \quad \text{Eq. 9}$$

The $\sin(\omega t)$ term can provide a better fit to data that has periodic spikes in response that commonly occur with every pump stroke as particulates are stirred up. Of course, this oscillating term prevents the curve from ever stabilizing to a fixed value no matter how long the time so it is not an asymptotic curve. The value of $\omega$ can be chosen to coincide with the pump-stroke frequency.

For Eq. 9, the present invention finds best $A_0$, $A_1$ using a linear least squares fit to the N data points, $(A_i, t_i^{-5/12}+k^{-1}\sin(\omega t))$.

As shown in FIG. 6, in a third embodiment, the present invention provides for a pattern recognition 610. As shown in FIG. 6, the present invention performs a pattern recognition for a trial-and-error estimate of $A_0$, rather than a direct calculation of $A_0$. In this embodiment, the pattern to be observed is the closest resemblance to a straight line as determined by the highest correlation coefficient, R, for a linear least squares fit. The method and apparatus performs a series of linear least squares fits to the absorbance data using a series of different estimates of $A_0$ starting with, $A+\epsilon$, $A+2\epsilon$, up to $A+N\epsilon$, where $A+N\epsilon<3.5$ OD, where 3.5 is used as an example for the upper dynamic range limit of the tool. The $A_0$ value for which the fit is closest to a straight line in log-log space then becomes the best estimate of $A_0$. Closeness of the fit to a straight-line shape is determined by the closeness of $R^2$ to unity, where $R^2$ is the correlation coefficient squared that ranges from 0 (no correlation) to 1 (perfect correlation). That is, for a series of $A_0$ guesses, find the best $A_0$ based on the best $R^2$ in a linear least squares fit to N measured data points, $(\log [t_i], \log [1-(A(t_i)/A_0)])$.

An example of the slope of such as line would be $(-p A_1/A_0)$, which for any fixed value of $p$, also allows immediate determination of $A_1$. One can assume a fixed value for $p$ or one can calculate a best-fit value for $p$ from the slope of the straight-line regression of $\ln(dA/dt)$ versus $\ln(t)$. Note that $A_0$ is not calculated here. Only $R^2$ is calculated for different guesses (estimates) of $A_0$. That is, different estimates of $A_0=A+n\epsilon$, are tried and the one that produces the best $R^2$ is used. To estimate $A_0$ to a finer resolution than $\epsilon$, one could use binary convergence to iteratively test $A_0$ values between the best two previously-determined $A_0$ values.

$$\log(1-f_{tp})=(-p)\log(t)+\log(A_1/A_0) \quad \text{Eq. 10}$$

For Eq. 10, for a series of different $A_0$ guesses, the present invention finds the best $R^2$ using a linear least squares fit to the N data points.

In a fourth embodiment, the method and apparatus of the present invention fits a differentiable curve to the measured data. The present invention estimates $f_{tp}$ from $(dA/dt)/A$ by fitting a continuously differentiable curve to the absorbance data (or smoothed absorbance data). A piecewise fit to various segments of the data can also be performed. Note that this fitting curve need not approach a terminal value itself. Its purpose is simply to provide a smooth fitting function over a large enough time interval of data points so that fitted values of both $A(t)$ and $dA(t)/dt$ can be calculated for any time, t, within the interval and then substituted into equations 14-16.

As shown in equations 14-16, the terminal absorbance value can now be determined from the ratio of the current slope, $dA(t)/dt$, to the current value, $A(t)$. The local fitting and smoothing functions used for calculating $dA(t)/dt$ and $A(t)$ do not need to have terminal values themselves. They can even tend to plus or minus infinity, at infinite time, as would occur with a power series fit or a group of power series fits.

Therefore, as shown in FIGS. 7, 8 and 9, without ever calculating $A_0$ or fitting an asymptotic curve to the absorbance data, it is possible to determine the fraction of terminal purity, $f_{tp}$, that is achieved at time, t from ratio of the rate of change of the absorbance to the absorbance.

For example, let $$A = A_0 - A_1 h(t) \quad \text{Eq. 11}$$

where $\lim_{t \to \infty} h(t) = 0$

Take first derivative with respect to time, $$(dA/dt)=-A_1(dh/dt) \text{ therefore } A_1=-(dA/dt)/(dh/dt) \quad \text{Eq. 12}$$

$$f_{tp}=A/[A+A_1 h(t)]=1/[1+A_1 h(t)/A]=1/[1-(dA/dt)(dh/dt)^{-1}h(t)A^{-1}] \quad \text{Eq. 13}$$

so $$f_{tp}=[1-A^{-1}(dA/ht)g(t)(dh/dt)^{-1}]^{-1} \quad \text{Eq. 14}$$

Example: Let $h(t)=t^{-p}$ so that $dh/dt=-pt^{-p}t^{-1}$ Then, $$f_{tp}=[1+A^{-1}(dA/dt)tp^{-1}]^{-1} \quad \text{Eq. 15}$$

For the special case where $p=5/12$, $$f_{tp}=[1+(12/5)A^{-1}(dA/dt)t]^{-1} \quad \text{Eq. 16}$$

In a fifth embodiment, as shown in FIG. 10, the method and apparatus of the present invention, finds terminal values of absorbance differences data rather than of absorbance itself. Absorbance differences of neighboring channels are plotted to remove baseline offsets caused by sand particles or bubbles 1010. The method and apparatus of the present invention perform a fit to absorbance differences rather than to absorbances themselves. The channel differences are forecast, for example, the difference between optical channels, OD16–OD15, corresponding to different optical wavelengths out to their terminal values, rather than forecasting a single OD channel out to its terminal value. The absorbance difference data is used independently or in conjunction with the approaches described in FIGS. 3-9 to determine fractional terminal purity, $f_{tp}$.

Figure 13:
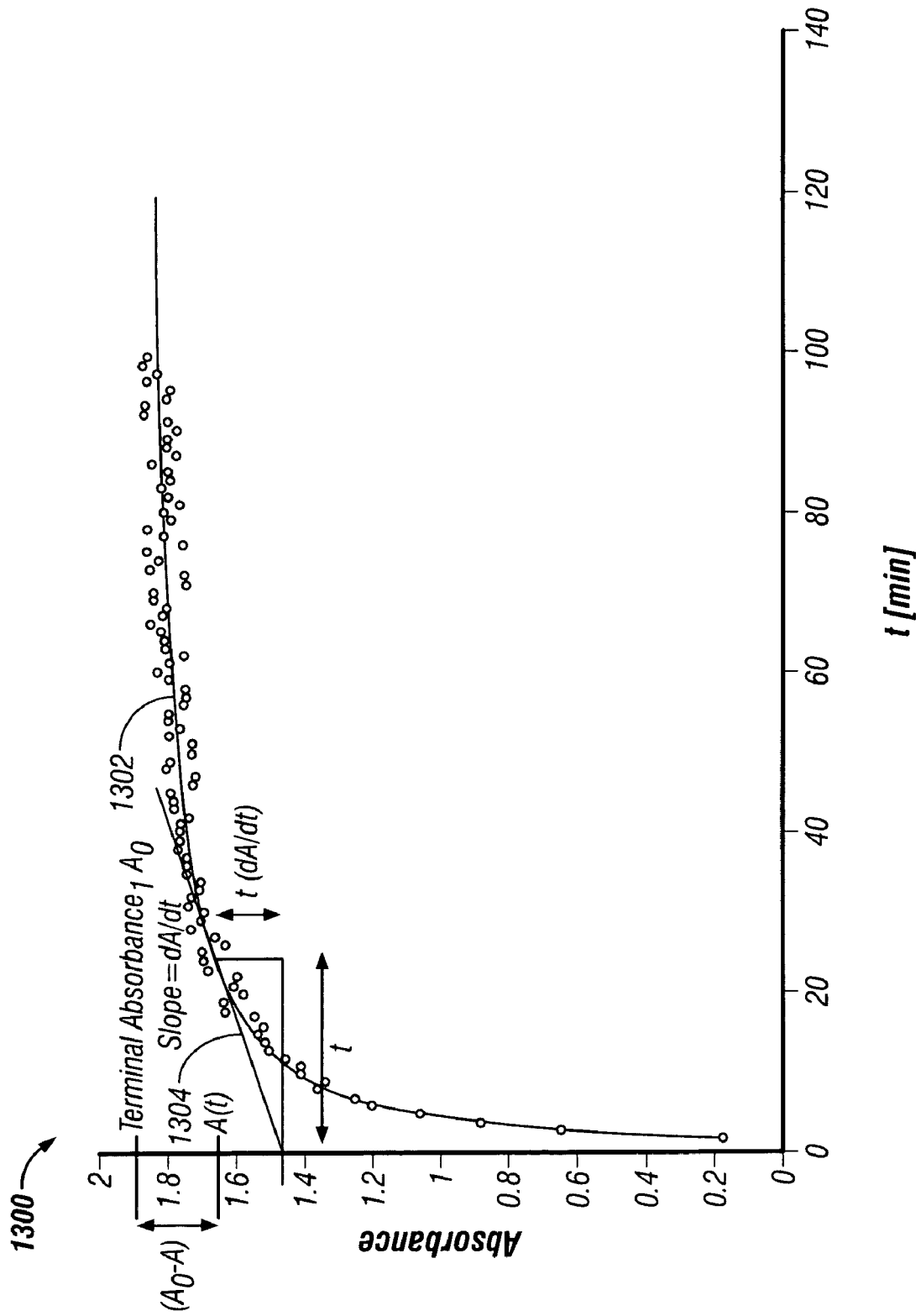
FIG. 13 is an illustration of an illustration of a function performed in another embodiment of the invention.

In a sixth embodiment, as shown in FIG. 13, we do not assume that "m" is a negative number, which is why the recursion formula is written as $[1+m(1+t/\Delta t)]$ instead of being written as $[1-m(1+t/\Delta t)]$. In the sixth embodiment, the closeness of the intercept "b" to zero is used. Closeness of the intercept to "b" is used because it is much more sensitive than the closeness of $R^2$ to unity for finding a best fit line when it is known that the intercept of that line should be zero. Also a recursive formula for predicting absorbance at future times is used. For data that falls and levels off over time, we use the absorbance at the left edge of the user-selected window as the starting absorbance rather than using zero as the starting absorbance as is done when the data rises and levels off.

In the sixth embodiment, as shown in FIG. 13, the present invention fits a continuously-differentiable, non-asymptotic curve 1302 to the raw data. The fit can be to the elapsed time or fit to the volume of fluid pumped. The present invention uses, for example, but is not limited to, fitting a non-asymptotic curve to the raw data points such as $A(t)=c_1+c_2 t^{1/2}+c_3 t^{1/3}+c_4 t^{1/4}$. Using calculus, we analytically calculate the first derivative as $dA/dt=(c_2/2)t^{-1/2}+(c_3/3)t^{-2/3}+(c_4/4)t^{-3/4}$. We call $A_0$ the "terminal" absorbance at some very long time (e.g., 24 hours) which is much longer than a time (2 hours) at which one would normally terminate pumping to achieve sample cleanup. As time progresses, both $(A_0-A)$ and t $(dA/dt)$ decrease, where A is absorbance at time t. Assuming that they decrease at the same rate, then they are proportional, which means $(A_0-A)=mt(dA/dt)$ where "m" is a constant. The present invention tries various guesses for $A_0$ until it finds a guess that produces the best linear, least-squares fit between $y=(A-A_0)$ and $x=[t(dA/dt)]$. The best fit is given by $y=mx+b$ where the intercept, b, is closest to zero, which we found to be more sensitive than finding the maximum $R^2$ for linear fits between two variables that are directly proportional. The present invention selects a raw data point at some time, t, (preferably, the latest time, t) at which the actual data intersects (or gets closest to) the best fit line. To forecast absorbance at a slightly later time, $t+\Delta t$, we use $\Delta A=(A_0-A)/[1+m(1+t/\Delta t)]$ which is obtained by replacing $dA/dt$ by $\Delta A/\Delta t$, replacing t by $t+\Delta t$, and replacing A by $A+\Delta A$ in $(A_0-A)=mt(dA/dt)$. We recursively apply this $\Delta A$ formula to forecast the absorbance at $t+\Delta t$ and then use our newly-calculated absorbance to compute the absorbance at some slightly later time, $t+2\Delta t$, and so on, for all future times.

If the slope 1304, m, of this fit is positive, it means a bad or undesirable section of raw data has been selected, which is curving upward or downward towards plus or minus infinity. Select a raw data point at some time, t, (preferably, the latest time, t) at which the actual data intersects (or gets closest to) the best fit line. The present invention then calculates the absorbance at some slightly later time, $A(t+\Delta t)=A(t)+\Delta A$, in terms of t, $A(t)$, $A_0$, and m using $\Delta A=(A_0-A)/[1+m(1+t/\Delta t)]$. The present invention then recursively applies this $\Delta A$ formula forward to generate future forecasts, $A(t)$, of the raw data. For data that is rising and leveling off over time, the fraction of terminal purity at any future time, t, is given by $A(t)/A_0$. For data that is falling and leveling off over time, the fraction of terminal purity at any future time, t, is given by $[A_S-A(t)]/[A_S-A_0]$. Here, $A_S$ is the starting absorbance at the left edge (the earliest time) of the user-selected data window.

Turning now to FIG. 11, a more detailed schematic of the pyroelectric array for determining mid-infrared spectra for the fluid is illustrated. In one embodiment, the present invention provides a light source 402, such as an infrared light source which can be a steady state light source or a modulated or pulsed light source. In the case of a steady state light source a light modulator is provided. The modulator can be any suitable device which varies the intensity of the light source, including but not limited to an electronic pulser circuit, well known in the art, that varies the intensity of the light source or an electromechanical chopper 404 that interrupts the path of the light source to the downhole fluid. The modulator is provided to modulate the intensity of light from the light source that impinges on the fluid and the photodetector. A reflector or collimator 403 can be provided to focus and/or concentrate light from the light source 402. A chamber or conduit 406 is provided for presentation of a downhole fluid for exposure of the downhole fluid to light from the light source. An optical window 408 is provided, through which the downhole fluid 407 is exposed to the light. For purposes of the present application, the term "fluid" includes liquids, gases and solids that may precipitate from a fluid or a gas.

The present invention further includes a detector such as a pyroelectric detector 412. The pyroelectric detector 412 can also comprise a pyroelectric detector array. A spectrometer 414 and processor 422 are provided for analyzing signals from the pyroelectric detector to determine a property of the fluid 407 downhole. A mid-infrared linear variable filter 416 is provided and interposed between light radiating 440 from the downhole fluid and the pyroelectric detector 412. A high gain amplifier 420 is provided to amplify the signal from the pyroelectric detector 412 when desired. The spectrometer 414 includes a processor 422 with memory. The processor 422 includes programs that implement soft modeling techniques for applying a chemometric equation, neural network or other soft modeling programs to the measurements of infrared light detected by the pyroelectric detector to estimate other physical and chemical properties of the downhole fluid from the pyroelectric detector signal. The spectrometer output responsive to the pyroelectric signal is also input to the soft modeling program, neural network or chemometric equation to estimate properties of the downhole fluid.

Turning now to FIG. 12, a more detailed schematic of the acoustic transducer for determining sound speed in the fluid is illustrated. The present invention provides a transducer 701, a sample flow line 703 or sample flow path 705 containing a fluid sample for measuring fluid density and sound speed of the fluid 708 inside of the tube or sample flow path or sample tank 711. The thickness 707 of the flow line wall 706 is known. A processor 702 and pulsing electronics 704 are provided to send an acoustic pulse from pulser 701*a* through wall 706 into fluid 705 in flow path 705 or from pulse 701*b* through wall 706 of thickness 707*b* to sample chamber 711. The transducer 701 receives echoes from the acoustic pulse, which are monitored by the processor. The present invention further comprises a wall standoff, which is an acoustic spacer interposed between the transducer and the wall that is made of the same material as the wall. This spacer simply increases the round trip distance and corresponding travel time for pulse-echo reverberations within the combined standoff plus near-wall material. It serves to lengthen the time between successive decaying echo pulses and so it serves to improve pulse separation, to avoid overlap of pulses and to improve quantification of energy in each pulse.

The processor determines the density of the fluid in the sample flow line. The present invention captures a fluid sample in a flow line from the formation or the borehole. The present invention then sends an acoustic pulse into the fluid sample in the flow line or sample tank. The processor of the present invention then monitors the echo returns within the wall of the flow line or sample tank and integrates the energy of each acoustic echo pulse. The processor determines the slope of the decay of the integrated acoustic echo pulses bouncing inside of the wall of the flow line. The present invention then determines the reflection coefficient for the inner wall/fluid interface. The present invention determines the speed of sound in the fluid. The present invention determines the density of the fluid in the line as described above. The present invention determines the viscosity of the fluid in the flow line as described above.

The present invention has been described as method and apparatus operating in a down hole environment in the preferred embodiment, however, the present invention may also be embodied as a set of instructions on a computer readable medium, comprising ROM, RAM, CD ROM, Flash or any other computer readable medium, now known or unknown that when executed cause a computer to implement the method of the present invention. While a preferred embodiment of the invention has been shown by the above invention, it is for purposes of example only and not intended to limit the scope of the invention, which is defined by the following claims.

What is claimed is:

1. A method for estimating a parameter of formation fluid downhole, comprising:
   extracting the fluid from a formation;
   making a plurality of measurements for a property, A, of the fluid;
   fitting a non-asymptotic curve to the plurality of measurements;
   taking a first derivative of the fitted curve; and
   selecting a terminal value of the property, $A_0$, that produces a best fit between y and x, wherein y=A at time t minus the terminal value, $A_0$, and x=t(dA/dt) at time, t; and
   estimating the parameter of the formation fluid using the best fit between y and x.

2. The method of claim 1, wherein the best fit is given by y=mx+b, where intercept, b is closest to zero and m is a slope.

3. The method of claim 2 further comprising:
selecting a data point which is close to the fitted curve and using its value, A, at time, t, for forecasting a future value of the property, A, at a later time, t+Δt.

4. The method of claim 3, wherein forecasting the property, A, at the later time further comprises determining $\Delta A=(A_0-A)/[1+m(1+t/\Delta t)]$.

5. The method of claim 4 further comprising:
   recursively determining ΔA for forecasting the property, A, at the later time.

6. The method of claim 1, wherein the property, A, is one of: (i) absorbance; (ii) fluorescence; (iii) refractive index; (iv) viscosity; (v) density; (vi) sound speed; and (vii) bulk modulus.

7. The method of claim 1, wherein the property of the fluid is formation fluid contamination.

8. An apparatus for use downhole, comprising:
   a probe for receiving a fluid from a formation;
   an optical sensor that makes a plurality of measurements of an optical property, A, of the fluid; and
   a processor configured to (i) fit the plurality of measurements of the optical property of the fluid to a non-asymptotic curve; (ii) take a first derivative of the fitted curve, and (iii) use one or more values of a terminal value of the optical property $A_0$, to produce a best fit between y and x, where y=the optical property, A, at time t, minus the terminal value, $A_0$, and x=t(dA/dt), at time t, and (iv) estimate a parameter of the formation fluid using the best fit between y and x.

9. The apparatus of claim 8 wherein the best fit is given by y=mx+b, and where intercept, b, is closest to zero and m is a slope.

10. The apparatus of claim 9, wherein the processor is further configured to select a data point which is close to the fitted curve and to use its value, A, at time, t, to forecast a future value of the optical property at a later time, t+Δt.

11. The apparatus of claim 10, wherein the processor is further configured to use $\Delta A =(A_0-A)/[1+m(1+t/\Delta t)]$ to forecast the future value of the optical property.

12. The apparatus of claim 11, wherein the processor is further configured to recursively determine ΔA to forecast the future value of the optical property.

13. The apparatus of claim 8, wherein the optical property, A, is one of: (i) absorbance; (ii) fluorescence; and (iii) refractive index.

14. A computer-readable-medium containing instructions that when executed by a computer perform a method for estimating formation fluid contamination downhole, comprising:
   extracting the fluid from a formation;
   making a plurality of measurements for a property, A, of the fluid over time; and
   fitting a non-asymptotic curve to the plurality of measurements of the property of the fluid;
   taking a first derivative of the fitted curve;
   using a terminal value of the property, Ao, to produce a best fit between y and x, wherein y=A, at time t, minus the terminal value, $A_0$, and x=t(dA/dt), and t=time; and
   estimating the formation fluid contamination at time, t, from the best fit between y and x.

15. The computer-readable-medium of claim 14, wherein in the method the best fit is given by y=mx+b, where intercept, b is closest to zero and m is a slope.

16. The computer-readable-medium of claim 15, wherein the method further comprises:
selecting a data point which is close to the fitted curve and using its value, A, at time, t, for forecasting a future value of the property, A, at a later time, t+Δt.

17. The computer-readable-medium of claim 16, wherein forecasting the property, A, further comprises determining $\Delta A=(A_0-A)/[1+m(1+t/\Delta t)]$.

18. The computer-readable-medium of claim 17, wherein the method further comprises:
   recursively determining ΔA to forecast the value of the property, A, for the future time.

19. The computer-readable-medium of claim 14, wherein the property, A, is one of: (i) absorbance; (ii) fluorescence; (iii) refractive index; (iv) viscosity; (v) density; (vi) sound speed; and (vii) bulk modulus.

* * * * *